United States Patent
O'Connor et al.

(10) Patent No.: US 8,362,434 B2
(45) Date of Patent: Jan. 29, 2013

(54) SYSTEM AND METHOD FOR RADIATION DOSE REDUCTION IN MOLECULAR BREAST IMAGING

(75) Inventors: Michael K. O'Connor, Rochester, MN (US); Carrie B. Hruska, Rocheser, MN (US)

(73) Assignee: MAYO Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 13/126,052

(22) PCT Filed: Nov. 3, 2009

(86) PCT No.: PCT/US2009/063111
§ 371 (c)(1),
(2), (4) Date: Apr. 26, 2011

(87) PCT Pub. No.: WO2010/051558
PCT Pub. Date: May 6, 2010

(65) Prior Publication Data
US 2011/0207986 A1      Aug. 25, 2011

Related U.S. Application Data

(60) Provisional application No. 61/110,639, filed on Nov. 3, 2008.

(51) Int. Cl.
*G01T 1/10*        (2006.01)
(52) U.S. Cl. .................................................. 250/361 R

(58) Field of Classification Search .............. 250/361 R, 250/362, 363.01–363.1
See application file for complete search history.

(56) References Cited

U.S. PATENT DOCUMENTS

2003/0076988 A1    4/2003    Liang et al.
2004/0015075 A1    1/2004    Kimchy et al.

FOREIGN PATENT DOCUMENTS

WO         2008/073897 A2      6/2008

OTHER PUBLICATIONS

Judy et al., "Molecular breast imaging with directly opposing compact gamma cameras," 2007, IEEE Nuclear Science Symposium Conference Record, vol. M20-1, pp. 4040-4043.*
Ling et al, "Smoothing low-SNR molecular images via anisotropic median-diffusion," 2002, IEEE Transactions on Medical Imaging, vol. 21, No. 4, pp. 377-384.*
International Search Report and Written Opinion under date of Jan. 6, 2010 in connection with PCT/US2009/063111.

* cited by examiner

*Primary Examiner* — Kiho Kim
(74) *Attorney, Agent, or Firm* — Quarles & Brady, LLP

(57) ABSTRACT

A system and method is provided for analyzing detector data acquired during molecular breast imaging (MBI) that reduces a patient's radiation does without a reduction in image quality. The method processes and combines initial images acquired by the two gamma-camera detectors of the MBI system to produce a hybrid or composite image set having reduced noise and improved contrast. The composite image provides image quality comparable to that of traditional MBI methods, but at a lower patient radiation dose.

20 Claims, 5 Drawing Sheets

SYSTEM AND METHOD FOR RADIATION DOSE REDUCTION IN MOLECULAR BREAST IMAGING

CROSS-REFERENCE TO RELATED APPLICATIONS

This application is based on, claims the benefit of, and incorporates herein by reference in their entirety, PCT International Application PCT/US2009/063111 filed on Nov. 3, 2009 and U.S. Provisional Application Ser. No. 61/110,639, filed Nov. 3, 2008, and entitled "SYSTEM AND METHOD FOR RADIATION DOSE REDUCTION IN MOLECULAR BREAST IMAGING."

FIELD OF THE INVENTION

The present invention relates to systems and methods for molecular breast imaging and, more particularly, to a system and method for reducing the dose of radioactivity to which a patient is subjected while preserving image quality.

BACKGROUND OF THE INVENTION

Breast cancer is one of the most common forms of cancer and a leading cause of cancer death. Breast cancer screening has been recommended for many decades and several large scale studies have demonstrated a clear benefit to screening, particularly for women over the age of fifty. The combination of early detection and improved therapy has resulted in a significant reduction in breast cancer mortality.

Despite the success of screening mammography, it is also recognized as a less than ideal screening method. The limitations of mammography are particularly evident in women with mammographically dense breasts. The reduced sensitivity of mammography with increasing mammographic density is compounded by the fact that increased breast density is a significant risk factor for breast cancer.

One method for improved breast cancer screening is molecular breast imaging (MBI). In this method, a single-photon radiopharmaceutical, such as Tc-99m sestamibi, is administered to a subject and the subject's breast is compressed between two small gamma camera detectors. Radiation emitted by the single-photon radiopharmaceutical is then detected by collimation. Though MBI has been shown to have a high sensitivity to small lesions, its application in routine breast cancer screen is limited by the radiation dose associated the radiotracer agent. A variety of radiotracers may be used for MBI, but all of these radiopharmaceuticals deliver a radiation burden that is an order of magnitude larger than that delivered to a patient from a screening mammograph. Further, radiation dose reduction by simply reducing the amount of radiopharmaceutical administered to the subject can lead to reduced image quality, since fewer photons strike the gamma cameras.

It would therefore be desirable to have a system and method for reducing subject radiation exposure in MBI without causing a significant reduction in image quality.

SUMMARY OF THE INVENTION

The present invention overcomes the aforementioned drawbacks by providing a system and method for creating molecular breast images using a reduced radiation exposure, yet yielding images having contrast and noise ratios comparable to molecular breast images created using significantly higher radiation exposures. In particular, a system and method is providing for selectively combining the images associated with each of the detector arrays of an MBI system to produce a composite molecular breast image reduced noise and preserved contrast.

In accordance with one aspect of the present invention, a molecular breast imaging system is disclosed that includes a first planar gamma detector positioned opposite a second planar gamma detector, each configured to receive photons emitted from a radionuclide present in a subject's breast that is positioned between the first and second gamma detectors. The molecular breast imaging system also includes a processor configured to produce a first detector image associated with photons received by the first gamma detector and a second detector image associated with photons received by the second gamma detector and apply a filter configured to selectively combine the first and second detector images to produce a composite molecular breast image having reduced noise compared to the first and second detector images. The filter is further configured to reduce noise in non-target regions and preserve contrast in target regions.

In accordance with another aspect of the present invention, a method for constructing a molecular breast image is disclosed that includes acquiring a first detector image associated with a first gamma detector and a second detector image associated with a second gamma detector. The method also includes selectively combining the first and second detector images to construct a composite molecular breast image by applying a filter configured to construct non-target regions of the composite molecular breast image by determining a mean of corresponding non-target regions of the first and second molecular breast images and form target regions of the composite molecular breast image by preferentially selecting signal from a target region of either the first or second detector image.

Various other features of the present invention will be made apparent from the following detailed description and the drawings

DESCRIPTION OF THE PREFERRED EMBODIMENT

Figure 1:
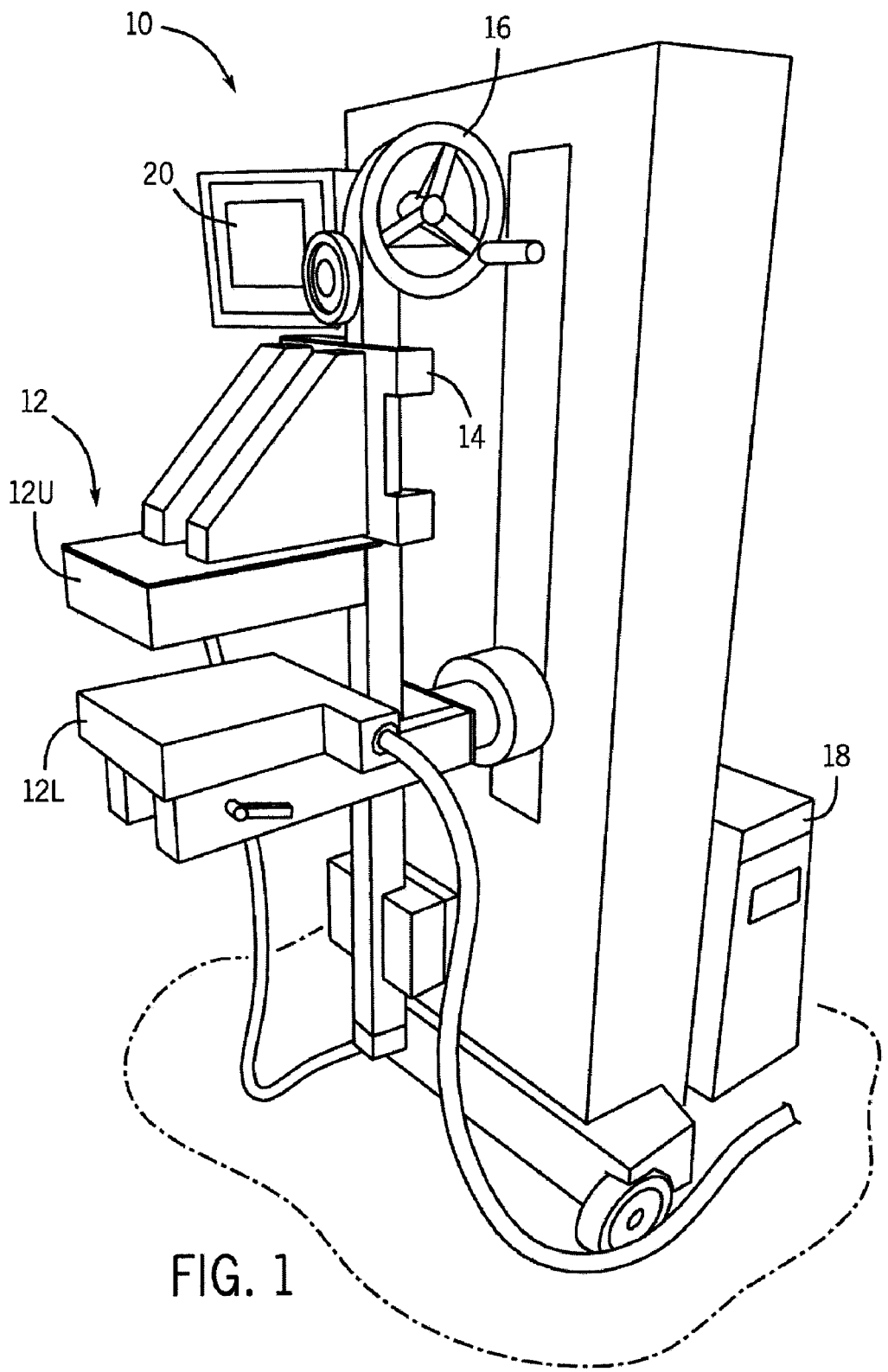
FIG. 1 is perspective view of an MBI imaging apparatus in accordance with the present invention.

Referring to FIG. 1, a molecular breast imaging system 10 includes two opposing detectors 12, for example, two cadmium zinc telluride (CZT) detectors (detector heads). In particular, the detector heads 12 include an upper detector head 12U and a lower detector head 12L. Each detector head 12U, 12L is, for example, 20 cm by 16 cm in size and mounted on a modified upright type mammographic gantry 14.

The relative position of the detector heads 12 can be adjusted using a user control 16. Specifically, the detector head assemblies 12 are, preferably, designed to serve as a compression mechanism. Accordingly, this system configuration reduces the maximum distance between any lesion in the breast and either detector head 12 to one-half of the total breast thickness, potentially increasing detection of small lesions without additional imaging time or dose. The MBI system 10 includes a processor 18 for processing the signals acquired by the detector heads 12 to produce an image, which may be displayed on an associated display 20.

To acquire breast images, a subject is injected with a radio-nuclide imaging agent, such as Tc-99m sestamibi. Preferably when the patient is seated, a breast is positioned between the detectors 12, and the breast is lightly compressed in order to improve image contrast and reduce motion artifacts. At around 5 minutes post-injection, the breast is imaged. The compression amount is approximately ⅓ that of conventional mammography and is typically pain free yet improves contrast and reduces motion artifacts. An image is acquired by each detector 12 (upper 12U and lower 12L) of each breast at each of two standard mammography views, for example craniocaudal (CC) and mediolateral oblique (MLO) positions, for 10 min/view. At each view, the upper and lower images are simultaneously acquired. Thus, for each breast, four images are obtained.

Figure 2:
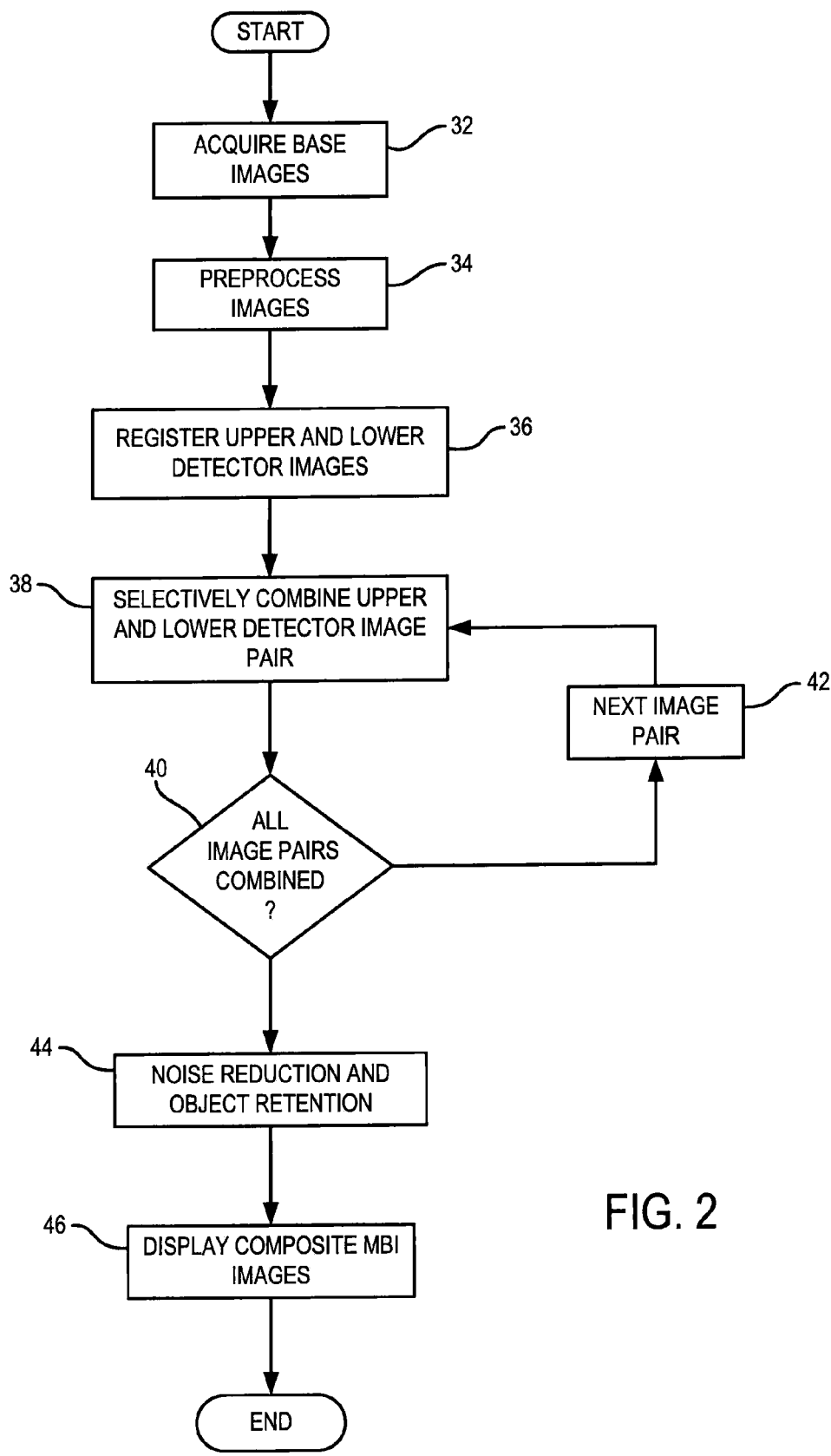
FIG. 2 is a flowchart setting forth the steps of an molecular breast imaging method using reduced subject radiation dose in accordance with the present invention.

Referring now to FIG. 2, a method for processing molecular breast images to reduce subject radiation dose begins at process block 32 with the acquisition of a set MBI base images using, for example, the MBI system 10 of FIG. 1. This generally involves administering a dose of radiotracer to the subject under study and positioning at least one of the subject's breasts between the gamma camera detectors of the MBI system. The photons emitted from the breast by the radiotracer can thus be acquired by the gamma cameras of the MBI system to produce a given pair of upper and lower detector images. Photons can be acquired from each breast at a plurality of angles to produce the set of MBI base images. For example, photons can be acquired with both the upper and lower detectors and from each breast at the CC and MLO positions to produce a set of eight base MBI images. While the upper and lower detector images of a breast at a given position may be similar, they are not identical. The appearance of a tumor in the detector images depend upon tumor depth or distance from the gamma camera detectors. Thus, a tumor closer to the lower gamma camera detector appears more intense in the lower detector image than in the upper detector image. Combination of the upper and lower detector images for a breast at given position can yield a single MBI image having reduced noise. However, this image may provide reduced tumor contrast if produced by simply taking the arithmetic or geometric mean of the upper and lower detector images. The contrast reduction is particularly prevalent in situations where a tumor is close to one gamma camera detector and far from the other. Accordingly, the present invention employs the following steps to generate composite MBI images with reduced noise levels without significantly reducing contrast.

Figure 3:
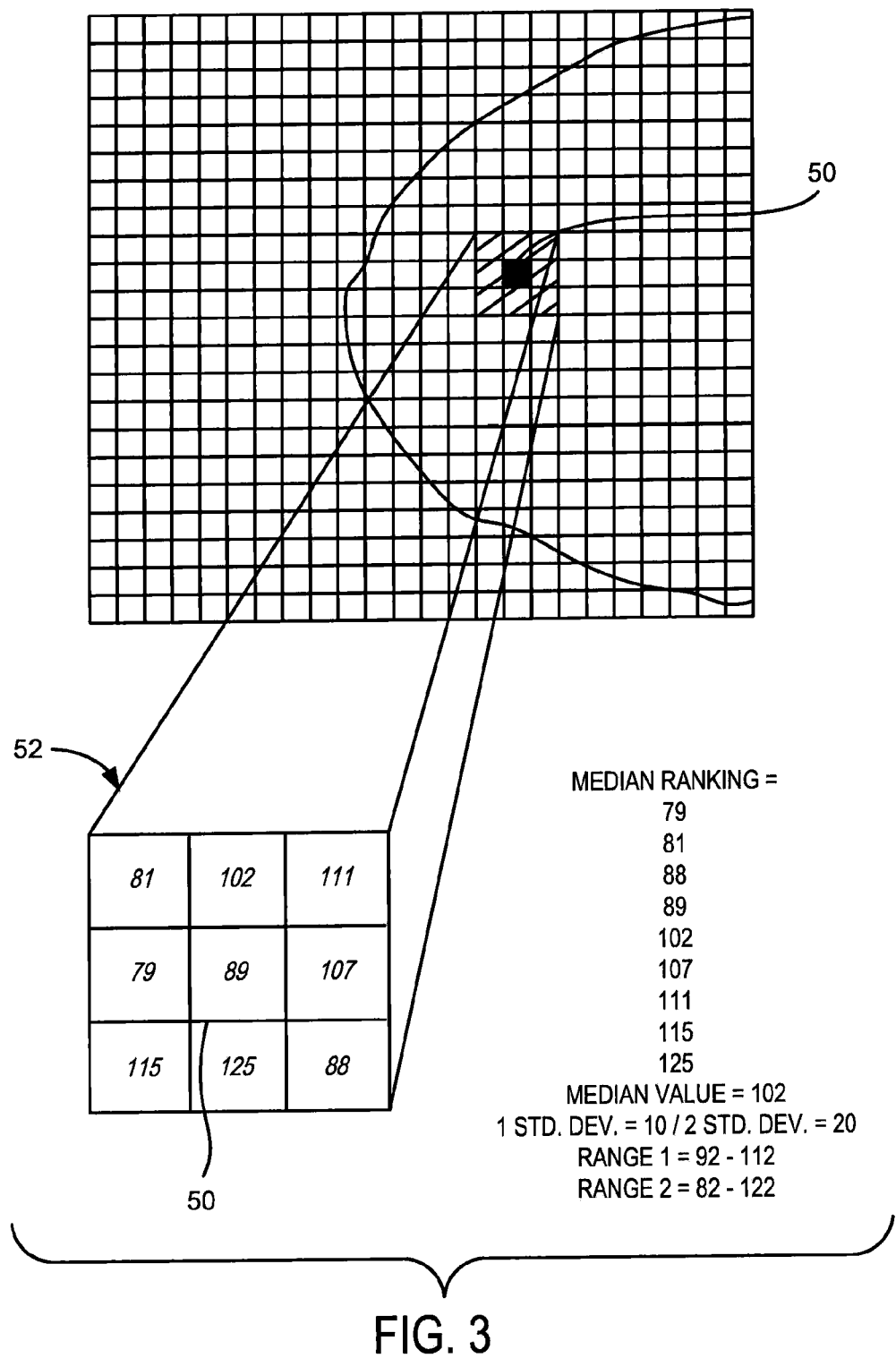
FIG. 3 is a schematic depiction of an order-statistics noise filtration method in accordance with the present invention.

Referring now to FIGS. 2 and 3, the MBI base images are individually preprocessed at process block 34 to reduce image noise prior to combining upper and lower detector image pairs. Preprocessing filters the MBI images to adjust the values of excessively noisy pixels, while retaining the lower noise content of the remaining pixels. Such filtration can be achieved in a number ways using a variety of filter types, such as Lee's local statistics filter, a Wiener filter, order-statistics filters, and other filters suitable for reducing the Poisson noise typically present in MBI images. In one approach to image preprocessing using an order-statistics filter, a median filter is applied to each MBI base image. The median value generated by the filter is then compared to pixel values in each respective image. If a selected pixel value is outside a specified range from the median value, then it is replaced with the closest value in the range. If the value falls within the specified range, the pixel is left unchanged. This order-statistics filtration is outlined in FIG. 3.

A selected pixel 50 having a value of 89 counts is preprocessed by analyzing a nine pixel array 52 that is centered on the selected pixel 50. The median value and standard deviation of the array 52 are calculated as 102 counts and 10 counts, respectively. Depending on the count density in a given region, the value of the selected pixel is compared to a range to determine if the pixel is excessively noisy and should be altered. The range can be determined as the median value plus or minus (F*SD), where F is a variable between one and three that adjusts for both high count density and low count density images. For the array 52, a value of F=1 provides a range of 92-112. Since the selected pixel 50 has a value 82 counts, which is outside of the 92-112 range, it is replaced by 92, the closest value within the range. For F=2, the value of the selected pixel falls within the range and is left unchanged.

Referring again to FIG. 2, the preprocessed MBI images are registered at process block 36 so that the corresponding upper and lower detector images for a given breast and given detector position are correctly aligned. Registration is performed using a correlation technique, in which one MBI image is shifted relative to its corresponding image by unit pixels until a shift producing the highest correlation value is reached. Typically, only minor shifts of the images are necessary.

At process block 38, the preprocessed and registered upper and lower detector image pairs are selectively combined to produce composite images having improved image quality. To ensure that noise reductions resulting from the combination of upper and lower detector images are not accompanied by a significant reduction in tumor contrast, the present invention employs a filter that takes the geometric mean of an upper and lower detector image pair in background regions, but preferentially keeps the larger values from a single detector in cases where a tumor is closer to that plate. To this end, and as will be described in further detail below, the filter is configured to construct non-target regions of the composite molecular breast image by determining a mean of corresponding non-target regions of the first and second molecular breast images and form target regions of the composite molecular breast image by preferentially selecting signal from a target region of either the first or second detector image. For example, a "target region" or "target tissue" may correspond to a likely tumor whereas "non-target regions" or "non-target tissue" may correspond to "background" or tissue likely to not correspond to a tumor.

The filter may be termed the "Gaussian neighborhood geometric mean" (GNGM) filter. The operation of the GNGM filter is based on the observation that regions in the upper and lower detector images having increased counts, for example, due to a tumor, are usually larger than a single pixel. A tumor significantly closer to one detector will therefore exhibit larger count values in the image associated with that detector than in the image associated with the opposing detector. Conversely, for background pixels, random noise will appear as a higher count in either the upper or lower detector image, but which image has the higher count will vary randomly across a neighborhood. Accordingly, if an entire neighborhood of points is systematically high in one detector image, then those are kept in the composite image. If the neighborhood shows random variations as to which detector image has the higher value, then the geometric mean of those values is used. Two exemplary methods for selectively combining the preprocessed and registered detector image pairs will be described in further detail below with reference to FIGS. 4 and 5.

At decision block 40, it is determined if all necessary detector image pairs have be combined. If not, then the filter proceeds to the next detector image pair at process block 42 and selectively combines the image pair at process block 38. If, at decision block 40, it is determined that no additional upper and lower image pairs should selectively combined, then the composite MBI images are filtered at process block 44 to further reduce noise while retaining, and not blurring, important information in the images. The preferred filter for achieving this is a non-local means (NLM) filter, which is based on self-similarity in the image and, for each pixel, calculates a filtered value based on a weighted average of other pixels within a large search region, with the weights determined by the similarity of the spatial neighborhoods of the two pixels. Prior to NLM filtration, Poission noise present in the composite MBI images can converted to Gaussian noise suitable for analysis by an NLM filter by the application of an Anscombe transform, which has an output given by output=$2\sqrt{\text{input}+3/8}$. This transformation is considered valid when the mean value of the Poisson data is greater than a selected threshold, for example, 20. Although this might not always be the case, particularly in the background regions of low dose scans, it is contemplated that filtering the transformed data generally provides improved noise reduction. A reverse Anscombe transform can be applied following NLM filtration to restore the Poisson-based noise distribution of the composite MBI images. It should be noted that the NLM filtering can instead be applied as part of the preprocessing of process block 42, rather than after selective combination.

The present invention displays the generated composite MBI images at process block 46. For example, four composite MBI could be generated by filtering a typical set of eight base MBI images in accordance with the present invention. The composite CC and MLO images for each breast have reduced noise in comparison with their parent images, but do not suffer from significantly reduced contrast.

Figure 4:
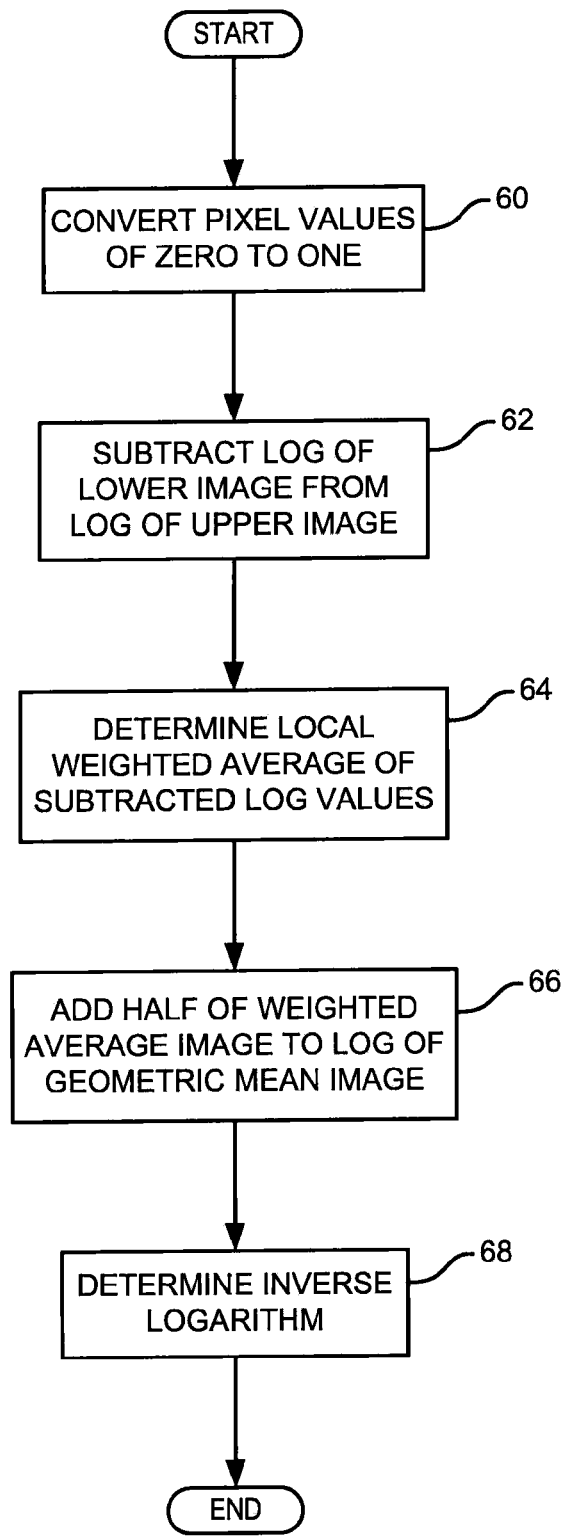
FIG. 4 is flowchart setting forth the steps of a method for selectively combining detector image pairs using a Gaussian neighborhood geometric mean filter in accordance with the present invention.

Referring now to FIG. 4, the GNGM filter which may be employed at process block 38 of FIG. 3 may be used to gradually transition between the case where composite image regions are formed from higher count values are taken preferentially from a single detector image and the case where larger count values in the detector image pair are attributed to noise in a detector image pair and the composite image region is formed as the geometric mean of the detector image pair. A method for achieving this begins at process block 60 with the conversion of zero-valued pixels in a detector image pair to pixels having a value of one so that the logarithm of all image pixels is defined. At process block 62, the logarithm of the lower detector image pixels is subtracted from the logarithm of the corresponding upper detector image pixels, that is, either log(upper image)−log(lower image) or log(upper image/lower image) is determined. At process block 64, the filter determines the weighted average of the resulting values over a selected neighborhood, for example, by smoothing the images with a Gaussian filter. Background regions of the resulting weighted average image should have a value close to zero. In regions containing a tumor that is closer to one of the detectors, the weighted average should vary significantly from zero depending on how much stronger the tumor signal is in one detector image compared to the other detector image.

It should be noted that a strong positive value in the weighted average generally indicates that the tumor is closer to the upper detector, while a strong negative value indicates that the tumor is closer to the lower detector.

At process block 66, half of the weighted average image is added to the logarithm of the geometric mean of the upper and lower detector images to produce a logarithmic composite image. That is, the logarithmic composite image is generated by calculating $$\frac{1}{2}(\text{weighted average image}) + \text{mean}(\log(\text{upper image}), \log(\text{lower image})).$$

If there were no neighborhood averaging, this would simply recover the value of the logarithm of the higher value. With neighborhood averaging, this image contains the log of the geometric mean in background regions, but is biased towards the log of higher count values in regions containing a tumor. For a large tumor closer to one detector, this value should be a somewhat averaged version of the log of the higher count values present in the detector image associated with the detector. At process block 68, the inverse logarithm of the logarithmic composite image is determined in order to obtain the composite MBI image. The GNGM filter thus combines a pair of upper and lower detector images using the following equation:

$$GNGM = e^{0.5(abs(G) + \log(H1) + \log(H2))} \qquad \text{Eqn. 1;}$$

where H1 and H2 are the upper and lower detector images, respectively, and G is an image of log(H1/H1) that has been filtered with a user-defined Gaussian kernel.

Figure 5:
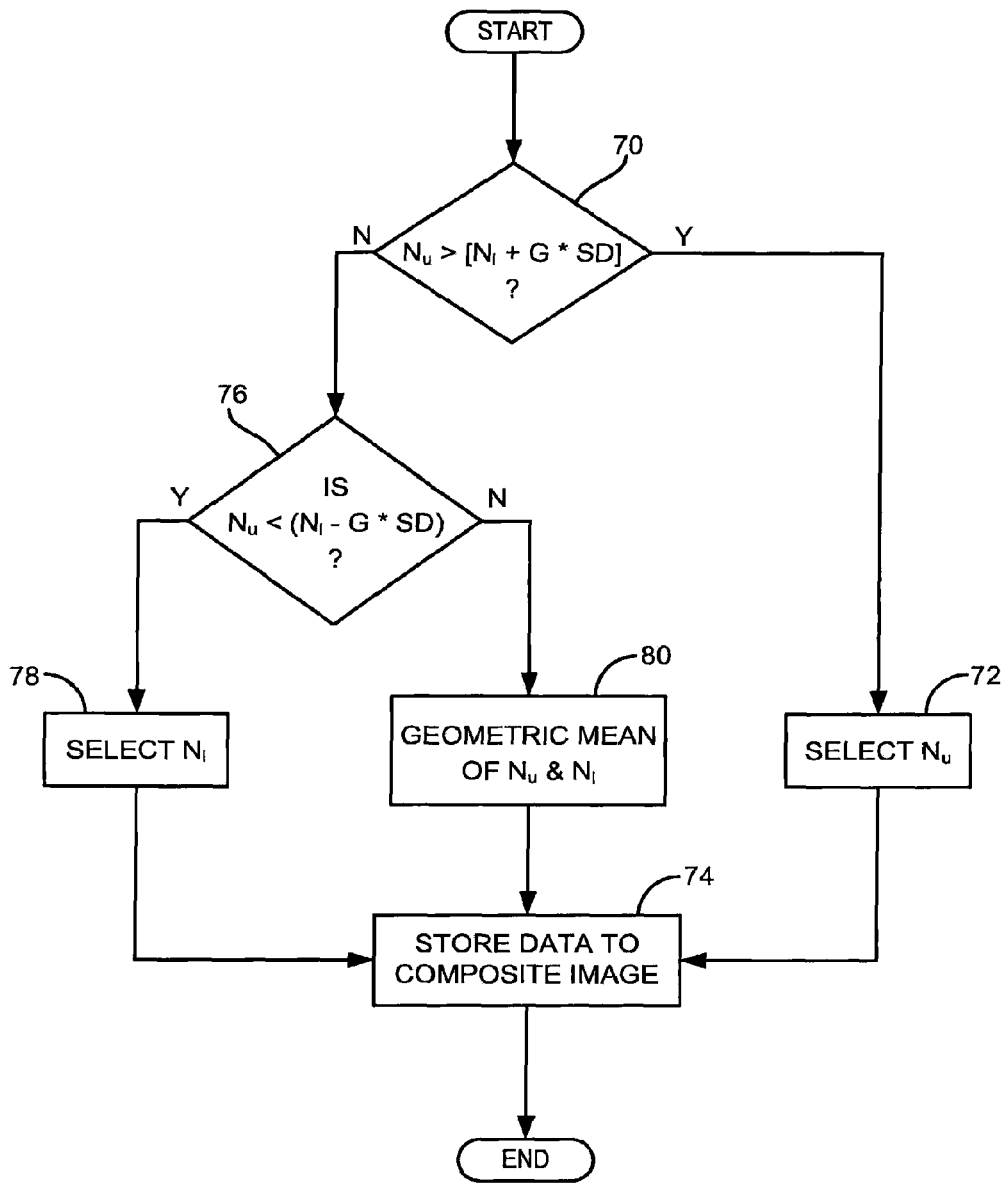
FIG. 5 is a flowchart setting forth the steps of a method for selectively combing detector image pairs using a geometric mean filtering scheme in accordance with the present invention.

Referring to FIG. 5, selective combination of the detector images can be achieved using an adaptive geometric mean image method that compares count values for corresponding pixel values in the upper and lower detector images, $N_U$ and $N_L$, respectively. Such a method begins at decision block 70, at which the value of a selected upper image pixel $N_U$ is compared to the value of the corresponding lower image pixel $N_L$ plus a deviation factor (G*SD) In this case, G is a variable between 1 and 2, and SD is the standard deviation of pixel values in the image. If $N_U$ is greater ($N_L$+G*SD), then the value of $N_U$ is selected at process block 72 and stored to the appropriate composite image at process block 74. If $N_U$ is less than ($N_L$+G*SD), then it is compared to $N_L$ minus the deviation factor at decision block 76. If $N_U$ is less than ($N_L$−G*SD), then it is selected at process block 78 and stored to the composite image at process block 74. If it is greater than ($N_L$−G*SD), that is, if $N_U$ belongs to the range of values from ($N_L$−G*SD) to ($N_L$+G*SD), then the geometric mean of $N_U$ and $N_L$ is determined at process block 80 and stored to the composite image at process block 74.

Composite MBI images produced in accordance with the present invention provide an image quality comparable to that obtained by a single-head breast imaging system with an acquisition time that is 2-3 times longer. Accordingly, these improvements can be translated into either shorter acquisition times or reduced subject radiation exposure doses, since an acceptable image quality can be achieved using a reduced dose of radiopharmaceutical. This is beneficial when performing breast cancer screening via MBI annually or biennially, because the reduction of per-scan radiation dose allowed by the present invention results in a significant reduction in cumulative radiation exposure over a number of years.

The present invention has been described in terms of one or more preferred embodiments, and it should be appreciated that many equivalents, alternatives, variations, and modifications, aside from those expressly stated, are possible and within the scope of the invention.

The invention claimed is:

1. A molecular breast imaging system comprising:
    a first planar gamma detector positioned opposite a second planar gamma detector, each configured to receive photons emitted from a radionuclide present in a subject's breast that is positioned between the first and second gamma detectors; and
    a processor configured to
        produce a first detector image associated with photons received by the first gamma detector and a second detector image associated with photons received by the second gamma detector and
        apply a filter configured to selectively combine the first and second detector images to produce a composite molecular breast image having reduced noise as compared to the first and second detector images,
        wherein the filter is configured to reduce noise in non-target regions and preserve contrast in target regions of said composite image.

2. The system as recited in claim 1, wherein the filter is an adaptive mean filter configured to
    form non-target regions of the composite molecular breast image by determining a mean of corresponding pixels in the first and second detector images and
    form target regions of the composite molecular breast image by preferentially selecting signal from either the first detector image or the second detector image.

3. The system as recited in claim 2 wherein the adaptive mean filter is configured to form non-target regions of the composite molecular breast image by preferentially selecting signal from the first detector image when an object depicted in the non-target region is closer to the first planar gamma detector than the second planar gamma detector.

4. The system as recited in claim 2 wherein the adaptive mean filter is configured to form non-target regions of the composite molecular breast image by preferentially selecting signal from the second detector image when an object depicted in the non-target region is closer to the second planar gamma detector than the first planar gamma detector.

5. The system as recited in claim 2 wherein the adaptive mean filter is a Gaussian neighborhood geometric mean filter.

6. The system as recited in claim 5, wherein the Gaussian neighborhood geometric mean filter is configured to:
    convert pixel values of zero in the first and second detector images to pixel values of one;
    subtract logarithms of the first and second detector images to produce a log difference image;
    determine a weighted average of the log difference image over a selected neighborhood;
    add a fraction of the weighted average of the log difference image to a logarithm of a geometric mean of the first and second detector images to produce a log composite image; and
    determine an inverse logarithm of the log composite image to produce the composite molecular breast image.

7. The system as recited in claim 2 wherein the adaptive mean filter is configured to:
    store, into the composite molecular breast image, pixel values of the first detector image that are greater than corresponding pixel values of the second detector image plus a deviation factor;
    store, into the composite molecular breast image, pixel values of the second detector image if corresponding pixel values of the first detector image are less than the pixel values of the second detector image minus a deviation factor; and
    store, into the composite molecular breast image, a geometric mean of equivalent pixel values of the first and second detector images for pixel values of the first detector image that are within a range defined by corresponding pixel values of the second detector image plus or minus a deviation factor.

8. The system as recited in claim 1 wherein the processor is further configured to register the first and second detector images prior to applying the filter configured to selectively combine the first and second detector images.

9. The system as recited in claim 1 wherein the processor is further configured to reduce image noise in the first and second detector images prior to applying the filter configured to selectively combine the first and second detector images.

10. The system as recited in claim 1 wherein the processor is further configured to apply a non-local means filter to the composite molecular breast image to reduce noise therein.

11. The system as recited in claim 1 wherein the reduced noise and preserve contrast of the composite molecular breast image allows at least one of a reduction in a dose of the radionuclide administered to the subject and reduce scan times.

12. A method for constructing a molecular breast image, the method comprising the steps of:
    a) acquiring a first detector image associated with a first gamma detector and a second detector image associated with a second gamma detector; and
    b) selectively combining the first and second detector images to construct a composite molecular breast image by applying a filter configured to
        construct non-target regions of the composite molecular breast image by determining a mean of corresponding non-target regions of the first and second detector images and
        form target regions of the composite molecular breast image by preferentially selecting signal from a target region of either the first or second detector image based at least in part on determination of whether neighborhoods of pixels representing the target regions in said first and second detector images provide systematically high photon counts or random variations of the photon counts.

13. The method as recited in claim 12 wherein step b) includes forming target regions of the composite molecular breast image by preferentially selecting signal from a target region the first detector image when a target object depicted in the target region is positioned closer to the first gamma detector than the second gamma detector.

14. The method as recited in claim 12 wherein step b) includes forming target regions of the composite molecular breast image by preferentially selecting signal from a target region the second detector image when a target object depicted in the target region is positioned closer to the second gamma detector than the first gamma detector.

15. The method as recited in claim 14 wherein step b) further includes:
    b) i) determining a difference of a logarithm of the first and second detector images to produce a log difference image;
    b) ii) determining a local weighted average of the log difference image;
    b) iii) adding a fraction of the local weighted average determined in step b) ii) to a logarithm of a geometric mean of the first and second detector images to produce a log composite image; and b) iv) determining an inverse logarithm of the log composite image to produce the composite molecular breast image.

16. The method as recited in claim 12 wherein step b) includes registering the the first and second detector images prior to applying the filter.

17. The method as recited in claim 12 wherein step b) includes preprocessing the first and second detector images to reduce image noise prior to applying the filter.

18. The method as recited in claim 17 further comprising step c) applying a non-local means filter to the composite molecular breast image to reduce image noise therein.

19. A molecular breast imaging system comprising:

first and second planar gamma detectors positioned opposite one another, each configured to receive photons emitted from a radionuclide present in a subject's breast that is compressed between the first and second gamma detectors; and a processor configured to produce a first two-dimensional (2D) image associated with photons received by the first gamma detector and a second 2D image associated with photons received by the second gamma detector;

identify, in each of the first and second 2D images, respectively corresponding first and second groups of pixels representing the same chosen portion of the imaged subject's breast;

apply an image data filter to form a composite 2D image of the subject's breast, said image data filter is configured to assign, to a group of pixels representing the same chosen portion of the imaged subject's breast in the composite 2D image, (i) values corresponding to a selected one of the first and second groups of pixels when said selected group of pixels provides a systematically higher count of photons across pixels of said selected group as compared to another of the first and second groups of pixels; and (ii) values corresponding to the geometric mean of the photon counts of the first and second groups of pixels when said selected group exhibits random variations of photons counts across pixels of said selected group, said image data filter further configured to reduce noise in non-target regions and preserve contrast in target regions of said composite 2D image as compared to the first and second 2D images.

20. The system as recited in claim 19, wherein the image data filter is configured to: convert pixel values of zero in the first and second 2D images to pixel values of one; subtract logarithms of the first and second 2D images to produce a log difference image; determine a weighted average of the log difference image over a selected neighborhood of pixels; add a fraction of the weighted average of the log difference image to a logarithm of a geometric mean of the first and second 2D images to produce a log composite image; and determine an inverse logarithm of the log composite image to produce the composite 2D image of the subject's breast.

* * * * *